(12) United States Patent
Brady et al.

(10) Patent No.: US 8,319,182 B1
(45) Date of Patent: Nov. 27, 2012

(54) METHODS AND SYSTEMS FOR USING IR SPECTROSCOPY TO QUANTIFY DEGRADATION OF WIRING INSULATION

(75) Inventors: Steven Kenneth Brady, Renton, WA (US); Paul H. Shelley, Lakewood, WA (US); Paul Griffin Vahey, Seattle, WA (US)

(73) Assignee: The Boeing Company, Chicago, IL (US)

( * ) Notice: Subject to any disclaimer, the term of this patent is extended or adjusted under 35 U.S.C. 154(b) by 303 days.

(21) Appl. No.: 12/844,025

(22) Filed: Jul. 27, 2010

(51) Int. Cl.
*G01R 31/02* (2006.01)
*G01J 5/02* (2006.01)

(52) U.S. Cl. .................... 250/339.07; 324/541; 324/544

(58) Field of Classification Search ............. 250/338.1, 250/339.07, 339.08; 324/541, 543, 544
See application file for complete search history.

(56) References Cited

U.S. PATENT DOCUMENTS

| | | | |
|---|---|---|---|
| 6,995,565 B1 * | 2/2006 | Tulloch et al. | 324/514 |
| 7,605,593 B2 | 10/2009 | Brady | |
| 7,612,325 B1 * | 11/2009 | Watkins et al. | 250/222.2 |
| 2005/0212526 A1 * | 9/2005 | Blades | 324/543 |
| 2008/0204034 A1 * | 8/2008 | Blades | 324/522 |

* cited by examiner

*Primary Examiner* — Mark R Gaworecki
(74) *Attorney, Agent, or Firm* — Armstrong Teasdale LLP

(57) ABSTRACT

A system for the measurement of degradation of electrical wire insulation is described. The system includes an infrared (IR) spectrometer, a fiber optic cable having a first end and a second end, where the first end is configured to interface to the IR spectrometer, and a clamping device for engaging the electrical wire to be tested for insulation degradation. The second end of said fiber optic cable is mounted within the clamping device such that the second end is adjacent the wire insulation.

22 Claims, 5 Drawing Sheets

METHODS AND SYSTEMS FOR USING IR SPECTROSCOPY TO QUANTIFY DEGRADATION OF WIRING INSULATION

BACKGROUND

The field of the disclosure relates generally to the service life of wiring insulation, and more specifically, to methods and systems for using infrared spectroscopy to quantify degradation of wiring insulation.

In service equipment may experience degradation in wiring systems that can lead to equipment failures, shorts, arcing, fires, and other operational and safety problems. One area where this degradation may occur is the various insulation and insulative coatings associated with the wiring systems. Of course, in many instances of in-service equipment, such equipment is exposed to extreme conditions (temperature, humidity, etc.) which may shorten the service life of the wiring systems associated with such equipment. Measurement of the condition of the wire insulation can verify whether or not replacement of the particular wire or wiring system is needed.

However, there are no known non-destructive inspection tests for the evaluation of wire insulation. Wire insulation testing devices do exist for directly measuring the resistance of wiring insulation, but these testing devices, including mega-ohm meters can be destructive to the wires being tested and generally involve the disassembly and repair of the wiring system being tested.

As such, some of the disadvantages and limitations of the existing wire insulation testing solutions include disruptive system disassembly, costly destructive testing and laboratory analysis, potentially premature wiring replacement, and an inability to predict remaining life of the wiring system and the insulation associated therewith. Thermal, oxidative (or "chemical"), and ultraviolet damage measurement of materials using infrared spectroscopy systems deployed within portable tools is known.

BRIEF DESCRIPTION

In one aspect, a system for the measurement of degradation of electrical wire insulation is provided. The system includes an infrared (IR) spectrometer, a fiber optic cable having a first end and a second end, the first end configured to interface to the IR spectrometer, and a clamping device for engaging the electrical wire to be tested for insulation degradation. The second end of the fiber optic cable is mounted within the clamping device such that the second end is adjacent the wire insulation.

In another aspect, a method for non-destructively measuring degradation of wire insulation is provided. The method includes placing the wire within a clamping device such that the wire is adjacent a first end of a fiber optic cable operatively fixed within the clamping device, impinging the wire insulation with an infrared signal through the fiber optic cable, a second end of the fiber optic cable operatively attached to an infrared (IR) spectrometer, and receiving a signal at the IR spectrometer, the signal reflected back through the fiber optic cable from the wire insulation, the reflected signal usable for determining an infrared absorbance of the wire insulation and therefore a degradation of the wire insulation.

In still another aspect, an apparatus for the non-destructive measurement of electric wire insulation degradation is provided. The apparatus includes a spring-hinged clamping fixture for holding the wire for which insulation degradation is to be measured, a fiber optic cable mounted within the clamping fixture having a first end and a second end, the first end operable for attachment to an infrared spectrometer, and at least one wire guide inserted into the clamping fixture. The wire guides include a channel formed therein for placement of the electric wire therein which is based on a wire gauge associated with the channel such that the second end of the fiber optic cable is adjacent the wire insulation upon insertion of the electric wire.

The features, functions, and advantages that have been discussed can be achieved independently in various embodiments or may be combined in yet other embodiments further details of which can be seen with reference to the following description and drawings.

DETAILED DESCRIPTION

Embodiments are described herein which relate to the non-destructive inspection of wiring insulation for degradation that can occur with age, thermal, or chemical exposure. Specifically, one embodiment of this testing device includes a wire clamp for connecting a fiber optic cable causing the fiber optic cable to extend from the wire (insulation) under test to a hand-held infrared (IR) spectrometer that is capable of determining a condition of the insulation on the wire.

The described non-destructive wiring insulation testing device provides a user with, for example, an "on-aircraft" nondestructive method to detect and quantify any detrimental aging conditions for wiring insulation. Embodiments allow this detection on individual wires by incorporating a wire clamping device to position the wire, and thus the insulation associated with the wire, proximate or adjacent a fiber optic measurement port. The IR device may be near-IR (e.g., 0.8-2.5 microns in wavelength) or mid-IR (e.g., 2.5-15.0 microns in wavelength). Near-IR fiber optic interfaces are more mature and robust technology than mid-IR fiber optic systems. However, either fiber optic interface allows for the detection and quantification of wiring insulation degradation without disassembly of the associated electrical circuit. While described in terms of near-IR and mid-IR, the described embodiments should not be construed to be so limited. Embodiments that utilize Quantum Cascade Laser IR, Dispersive IR, Encoded Photometric Infrared (EPIR) and others are contemplated.

Figure 1:
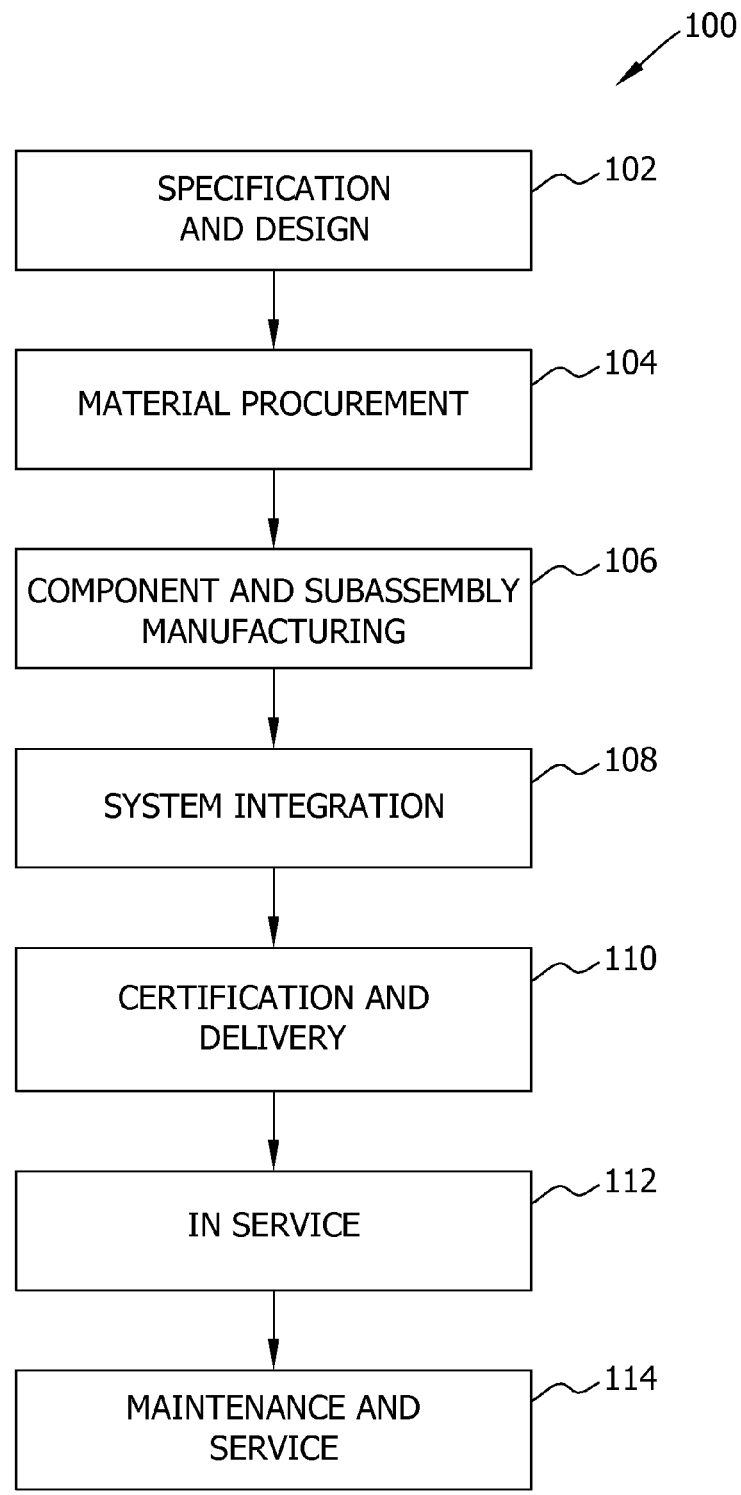
FIG. 1 is a flow diagram of an aircraft production and service methodology.
Figure 2:
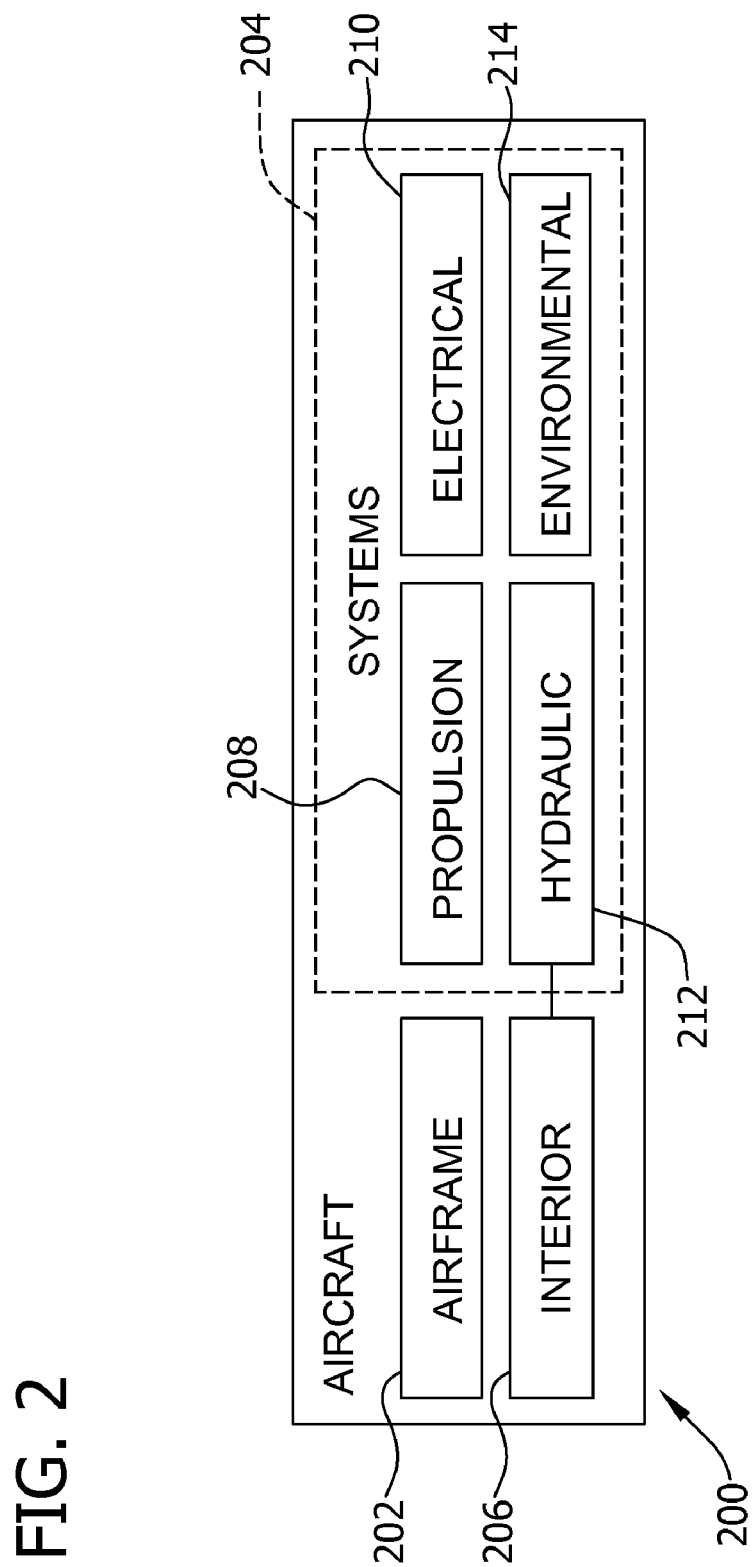
FIG. 2 is a block diagram of an aircraft.

Referring more particularly to the drawings, embodiments of the disclosure may be described in the context of aircraft manufacturing and service method 100 as shown in FIG. 1 and an aircraft 200 as shown in FIG. 2. During pre-production, aircraft manufacturing and service method 100 may include specification and design 102 of aircraft 200 and material procurement 104.

During production, component and subassembly manufacturing 106 and system integration 108 of aircraft 200 takes place. Thereafter, aircraft 200 may go through certification and delivery 110 in order to be placed in service 112. While in service by a customer, aircraft 200 is scheduled for routine maintenance and service 114 (which may also include modification, reconfiguration, refurbishment, and so on).

Each of the processes of aircraft manufacturing and service method 100 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 2, aircraft 200 produced by aircraft manufacturing and service method 100 may include airframe 202 with a plurality of systems 204 and interior 206. Examples of systems 204 include one or more of propulsion system 208, electrical system 210, hydraulic system 212, and environmental system 214. Any number of other systems may be included in this example. Although an aerospace example is shown, the principles of the disclosure may be applied to other industries, such as the automotive industry or the electrical power generation and distribution industries.

Apparatus and methods embodied herein may be employed during any one or more of the stages of aircraft manufacturing and service method 100. For example, without limitation, components or subassemblies corresponding to component and subassembly manufacturing 106 may be fabricated or manufactured in a manner similar to components or subassemblies produced while aircraft 200 is in service.

Also, one or more apparatus embodiments, method embodiments, or a combination thereof may be utilized during component and subassembly manufacturing 106 and system integration 108, for example, without limitation, by substantially expediting assembly of or reducing the cost of aircraft 200. Similarly, one or more of apparatus embodiments, method embodiments, or a combination thereof may be utilized while aircraft 200 is in service, for example, without limitation, to maintenance and service 114 may be used during system integration 108 and/or maintenance and service 114 to determine whether parts may be connected and/or mated to each other.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Figure 3:
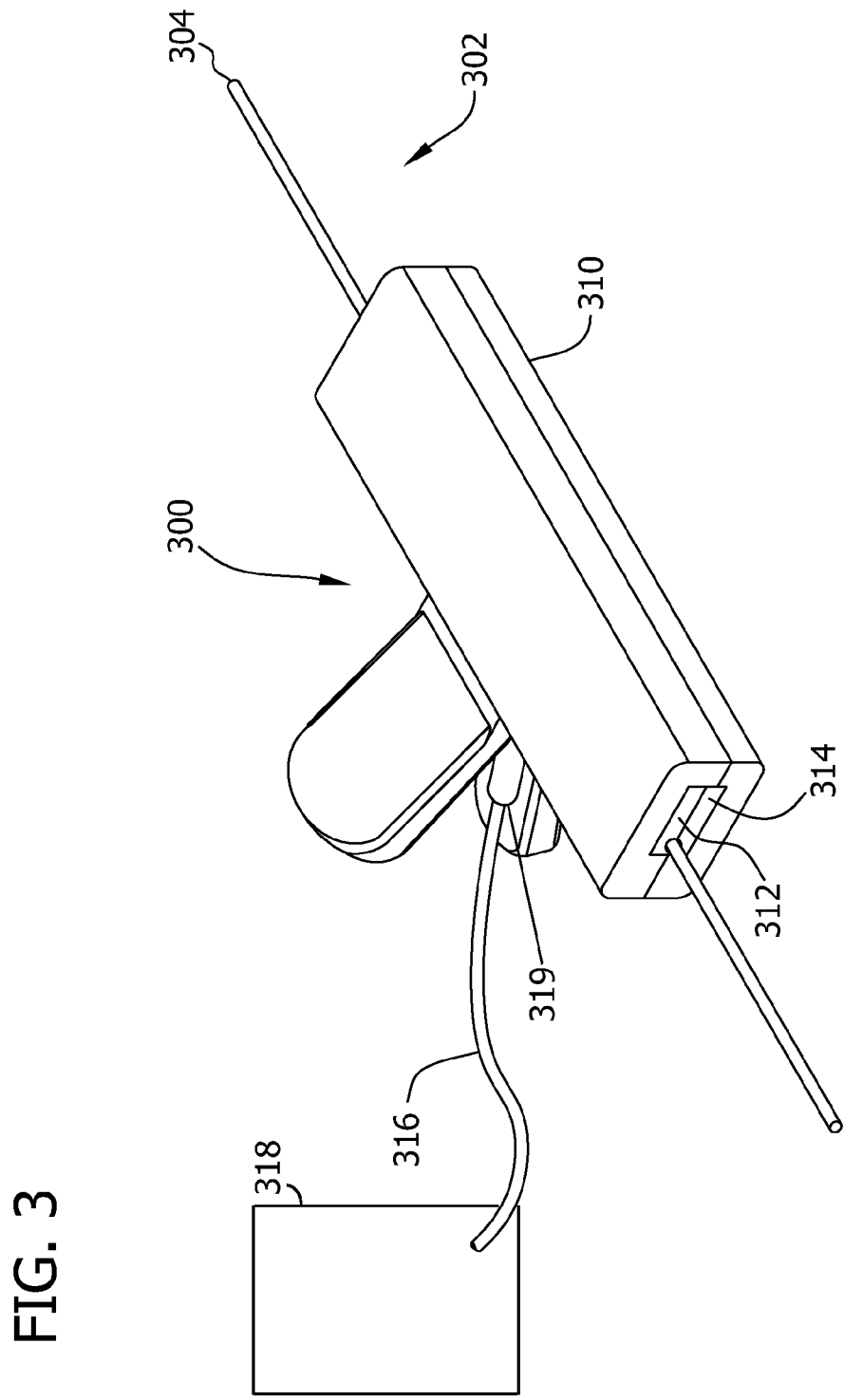
FIG. 3 is a diagram of a system for interfacing an infrared spectrometer for the measurement of wire insulation degradation.

As described above, existing wire insulation testing solutions sometimes include removal and sectioning of the wiring in order to perform laboratory-based testing. On-site testing of wire insulation sometimes involves disconnecting the wire from the circuit. If the wire and insulation pass the tests, it is put back into service. However, such handling of wires is time consuming and the possibility of wire and/or wire insulation damage exists. It is apparent that a non-destructive, in circuit testing solution would be an improvement. FIG. 3 is an illustration of a clamp 300 that allows for in circuit, nondestructive testing of the insulation 302 associated with wire 304. Clamp 300 allows for wiring insulation degradation testing without disassembly of the associated electrical circuit. The embodiments of clamp 300 allow for a nondestructive analysis that may be performed, for example, on wiring within an aircraft during a periodic maintenance process. Removal of the need to disassemble the electrical circuit containing wire 304 (and insulation 302) greatly reduces maintenance costs. In addition, tests may be conducted on the wire insulation 302 while the circuits associated with the wire 304 are energized, which, in certain circuit types, allows for additional testing methodologies to be developed. Removal of the need to disassemble the electrical circuit containing the wiring to be tested also increases safety for the inspector of the wiring insulation, reducing the risk of electrical shock.

Embodiments of clamp 300 include a clamp style probe 310, interchangeable wire-guide inserts 312, 314 for installation within probe 310, a fiber optic cable 316, and a portable IR spectroscopy device 318. Wire-guide inserts 312, 314 are interchangeable to accommodate different wire diameters while ensuring an end of fiber optic cable 316 within probe 310 is adjacent the insulation to be tested. Alternative embodiments may include a circuit (not shown in FIG. 3) disposed within probe 310, and an electrical signal cable (not shown in FIG. 3) interconnecting the circuit and an external device. As illustrated in the figures, a channel 319 may be formed in clamp 300 for retention of the fiber optic cable 316 within the clamp 300.

In exemplary embodiments, portable IR spectroscopy device 318 is one of the Phazir (near-IR) (www.polychromix.com) or Exoscan (Fourier transform mid-IR) (www.a2technologies.com) spectroscopy devices.

Clamp 300, together with portable IR spectroscopy device 318 nondestructively detects and quantifies the state of wiring insulation by determining an infrared spectrum associated with wire insulation 302. In use, probe 310 is clamped onto wire 304 to insure good contact or proximity between the wire insulation and the fiber optic cable 316, which is coupled, for example, to a spectrometer. The portable spectrometer uses this contact or proximity to interrogate the insulation with infrared light, to obtain an infrared IR spectrum associated with the wire insulation 302. A calibration to known good and bad wiring insulation (e.g., spectrum data associated with such insulation) is used to evaluate the wire insulation whose spectrum is being measured and such measurement of an aging state of the wiring insulation is displayed on the portable system or forwarded to another user interface or storage device.

Figure 4:
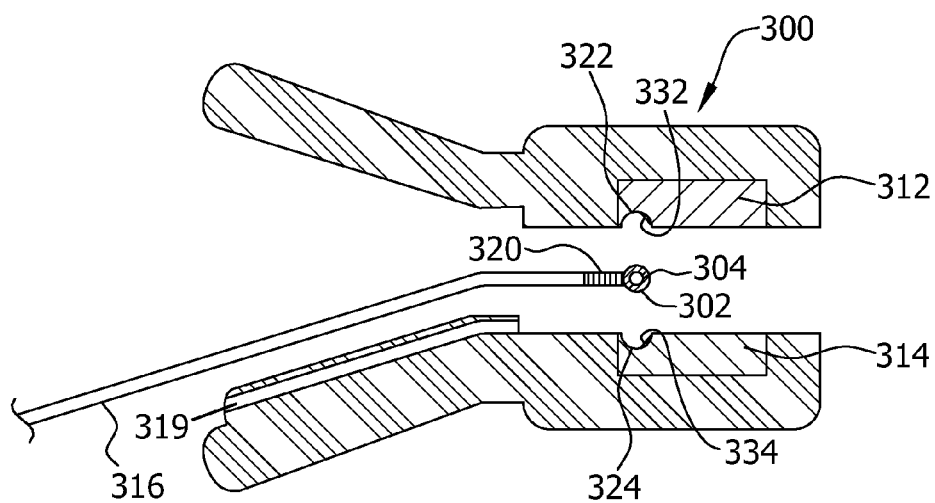
FIG. 4 is a side cutaway view of a clamp illustrating a pair of wire guide inserts for a first wire gauge range mounted therein.
Figure 5:
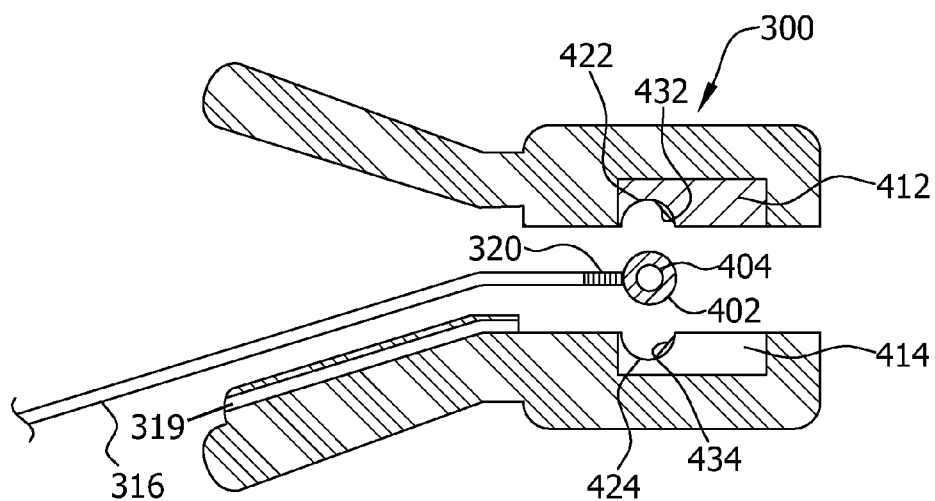
FIG. 5 is a side cutaway view of the clamp of FIG. 4 illustrating a different pair of wire guide inserts for a second wire gauge range mounted therein.

FIGS. 4 and 5 are side cutaway views of clamp 300 which further illustrates that fiber optic cable includes, for example, a sampling device 320 attached at an end thereof. Sampling device 320 is typically one of a diffuse reflectance device, a transmissive device, and an attenuated total reflectance (ATR) device. A transmissive device is part of a system that incorporates transmission measurements, which is contemplated for shorter near infrared (NIR) wavelengths. Referring again to FIGS. 4 and 5, in certain embodiments, sampling device 320 is placed within clamp 300 such that it is adjacent to or in contact with the wire insulation to be tested as further described herein. In FIG. 4, wire guide inserts 312 and 314 each have respective semi-circular wire guides 322 and 324 formed therein for insertion of wire 304 and its insulation 302. As is understood, semi-circular wire guides 322 and 324 operate within clamp 300 to retain wire 304 and insulation 302 in a specific location with respect to sampling device 320 of fiber optic cable 316. Specifically, semi-circular wire guides 322 and 324 are operative for a range of wire gauges such that the insulation 302 is substantially adjacent sampling device 320 for wire samples placed within clamp 300. In embodiments, semi-circular wire guides 322 and 324 are approximately equal to the outer diameter of the wire insulation. In embodiments, semi-circular wire guides 322 and 324 are each further configured to include a flat portion 332 and 334 respectively. These flat portions 332 and 334 are sized such that clamp 300 cannot completely close when a wire 304 and insulation 302 sample is placed therein. These flat portions 332 and 334 engage the wire insulation 302 as clamp begins to close and operates to push against the wire insulation 302 such that it tends to move towards and/or into good contact with the sampling device 320 associated with the fiber optic cable 316.

During the test, IR spectrometer 318 measures the changes that occur in reflected infrared light when the beam comes into contact with a sample of wire insulation. Infrared light from IR spectrometer 318 is directed through fiber optic cable 316 onto sampling device 320, which in embodiments includes ATR device having an optically dense crystal with a high refractive index at a certain angle. This internal reflectance creates a wave that extends beyond the surface of sampling device 320 and into the wire insulation sample held in contact with sampling device 320 by clamp 300. The wire insulation 302 will reflect a light back through the sampling device 320 and thus the fiber optic cable 316 for reception by IR spectrometer 318 that is indicative of the condition of the wire insulation 302. For example, this wave is modified due to some of the light being absorbed by the wire insulation 302. The amount of light absorbed at key wavelengths, and the ratios between the amount of light absorbed at these key wavelengths is indicative of the condition of the wire insulation 302.

In embodiments, fiber optic cable 316 may include a surrounding jacket, such as a woven stainless steel jacket which protects the cable 316. At the interface between cable 316 and IR spectrometer 318 focusing optics are utilized to get the light into and out of the fiber optic cable 316 from and to the IR spectrometer 318.

FIG. 5 is a side cutaway view of clamp 300 with a different set of wire guide inserts 412 and 414 placed therein. As is apparent from FIG. 5, wire guide inserts 412 and 414 are formed to include semi-circular wire guides 422 and 424 which are significantly larger in radius than are semi-circular wire guides 322 and 324. As such, semi-circular wire guides 422 and 424 are operative for a range of wire gauges that is larger in diameter, specifically, wire 404 and its insulation 402. The semi-circular wire guides 422 and 424 are offset somewhat as compared to semi-circular wire guides 322 and 324 which allow the fiber optic cable 316 to be similarly adjacent insulation 402. Similar to wire guides 322 and 324 described above, wire guides 422 and 424 are approximately equal to the outer diameter of the wire insulation of the larger wire. Embodiments of semi-circular wire guides 422 and 424 are also configured to each include a flat portion 432 and 434 respectively which operates in the same manner as flat portions 332 and 334 (shown in FIG. 4). Specifically, flat portions 432 and 434 engage the wire insulation 402 as clamp 300 begins to close and operates to push against the wire insulation 402 such that it tends to move towards and/or into good contact with the sampling device 320 associated with the fiber optic cable 316. While FIGS. 4 and 5 illustrate two embodiments of wire guide inserts, other embodiments are contemplated.

Figure 6:
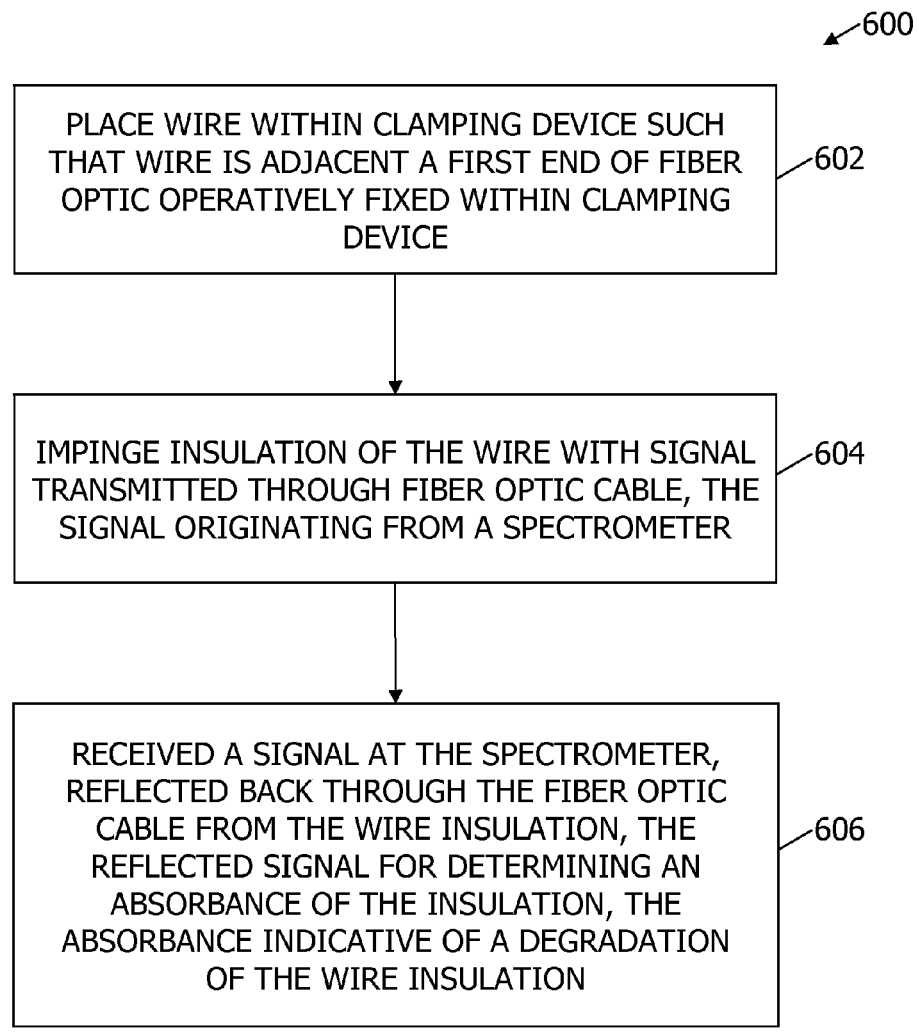
FIG. 6 is a flowchart illustrating a method for non-destructively measuring degradation of wire insulation.

Based on the embodiments described above, a method for non-destructively measuring degradation of wire insulation 302 is provided, as illustrated by the flowchart 600 of FIG. 6. Initially, a wire is placed 602 within a clamping device such that the wire is adjacent a first end of a fiber optic cable operatively fixed within the clamping device. The wire insulation 302 is impinged 604 with an infrared signal through the fiber optic cable, the second end of the fiber optic cable being operatively attached to an infrared (IR) spectrometer. A signal is then received 606 at the IR spectrometer. The received 606 signal is a signal that has been reflected back through the fiber optic cable from the wire insulation 302 and is usable for determining an infrared absorbance, and therefore a degradation of the wire insulation 302. As described elsewhere, the method may be practiced at an in service location of the wire using a portable spectrometer.

As described above, an infrared IR spectrum associated with the wire insulation 302 is obtained. The obtained spectrum is compared against IR spectrums associated with known good wire insulation and known bad (degraded) wire insulation of the same insulation type to evaluate the wire insulation being tested. These stored spectrums may be referred to as measurement models. In one embodiment, the IR spectrometer, or another device, retains such models for various insulation types and thicknesses. Such models may be further dependent on the particular wavelength of infrared light used. Further, specific measurement models for various wire insulations may be dependent on the sampling device 320 used with the fiber optic cable, with different measurement models (e.g., known spectrums for good insulation and degraded insulation) associated with diffuse reflectance devices, transmissive devices, and attenuated total reflectance devices as well as the wavelength of the light used with the known good and degraded insulation. As described above, the reflected IR spectrum is indicative of a modified amount of reflected IR light due to some of the light being absorbed by the wire insulation 302.

The above described embodiments nondestructively detect the aging state of wiring by reading the IR spectrum of the wire insulation. As described, the clamp 300, with the proper wire guide inserts placed therein, is clamped onto a wire to insure good contact of the wire insulation with the fiber optic cable and thus to the IR spectrometer that determines the spectrum of the wire insulation. A calibration to known spectra for good wire insulation and bad wire insulation is used to evaluate the wire being tested and therefore provide a measure of the aging state of the insulation. Such measure may then be displayed on the spectrometer, for example, a hand-held spectrometer system.

Using the embodiments, wiring condition can be verified nondestructively (i.e. without system and circuit disassembly) to avoid replacement if replacement is not needed. Aged wiring with poor insulation quality can be replaced before it causes problems. Costly and time consuming laboratory analysis of wire samples from the system incorporating the wire being tested is avoided.

An ability to monitor aging conditions in polymeric components in turn leads to a reduction in total ownership costs of systems that incorporate such wiring, such as aircraft systems and other aerospace applications. This device is also useful in determining the degradation state of other polymeric items with circular cross section, for example, plastic piping.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for the measurement of degradation of electrical wire insulation, said system comprising:
   an infrared (IR) spectrometer;
   a fiber optic cable comprising a first end and a second end, said first end configured to interface to said IR spectrometer; and
   a clamping device for engaging the electrical wire to be tested for insulation degradation, said second end of said fiber optic cable mounted within said clamping device such that said second end is adjacent the wire insulation.

2. The system according to claim 1 further comprising a plurality of interchangeable wire-guide inserts insertable within said clamping device, said interchangeable wire-guide inserts operable for maintaining a placement of a specific range of wire gauges within said clamping device.

3. The system of claim 2 wherein said interchangeable wire-guide inserts each comprise a semi-circular channel therein for placement of the wire, said semi-circular channels located within said wire guide inserts such that the wire is proximate said second end of said fiber optic cable.

4. The system according to claim 1 further comprising a sampling device operatively attached to said second end of said fiber optic cable.

5. The system according to claim 1 wherein said sampling device comprises one of a reflectance device, a transmissive device, and an attenuated total reflectance device at said second end of said fiber optic cable.

6. The system according to claim 1 wherein said IR spectrometer comprises at least one of a near infrared device and a mid infrared device.

7. The system according to claim 1 wherein said IR spectrometer comprises a portable device.

8. The system according to claim 1 wherein said clamping device comprises a spring tending to maintain said clamping device in a closed orientation.

9. The system according to claim 1 further comprising measurement models for various wire insulation types, said system comprising a processing device operable to compare an infrared absorbance of the wire insulation as measured by said IR spectrometer against a selected measurement model for determining a condition of the wire insulation.

10. The system according to claim 1 wherein said IR spectrometer is calibrated to estimate degradation changes in the wire insulation.

11. The system according to claim 1 further comprising a plurality of interchangeable wire-guide inserts insertable within said clamping device, said interchangeable wire-guide inserts each comprising a semi-circular channel therein for placement of the wire, at least one of said semi-circular channels including a flat portion formed therein operable to engage the wire insulation as said clamping device begins to close and push against the wire insulation such that the wire insulation tends to move towards said second end of said fiber optic cable.

12. A method for non-destructively measuring degradation of wire insulation, said method comprising:
   placing the wire within a clamping device such that the wire is adjacent a first end of a fiber optic cable operatively fixed within the clamping device;
   impinging the wire insulation with an infrared signal through the fiber optic cable, a second end of the fiber optic cable operatively attached to an infrared (IR) spectrometer; and
   receiving a signal at the IR spectrometer, the signal reflected back through the fiber optic cable from the wire insulation, the reflected signal usable for determining an infrared absorbance of the wire insulation and therefore a degradation of the wire insulation.

13. The method of claim 12 wherein placing the wire within a clamping device comprises inserting a set of wire-guide inserts within the clamping device, each set of wire-guide inserts operable for maintaining a placement of a wire, within a specific range of wire gauges, adjacent the first end of the fiber optic cable.

14. The method of claim 12 wherein placing the wire within a clamping device comprises placing the clamping device on the wire at an in service location of the wire.

15. The method of claim 12 further comprising comparing the infrared absorbance of the wire insulation against a selected measurement model for determining a condition of the wire insulation.

16. The method of claim 12 wherein impinging the wire insulation with an infrared signal through the fiber optic cable comprises impinging the wire insulation with at least one of a near infrared signal and a mid infrared signal.

17. The method of claim 12 wherein impinging the wire insulation with an infrared signal through the fiber optic cable comprises impinging the wire insulation through a sampling device located at the first end of the fiber optic cable.

18. The method of claim 12 wherein the sampling device is one of a reflection device, a transmissive device, and an attenuated total reflectance device.

19. Apparatus for the non-destructive measurement of electric wire insulation degradation, said apparatus comprising:
   a spring-hinged clamping fixture for holding the wire for which insulation degradation is to be measured;
   a fiber optic cable mounted within said clamping fixture, said fiber optic cable comprising a first end and a second end, said first end operable for attachment to an infrared spectrometer; and
   at least one wire guide inserted into said clamping fixture, said at least one wire guide comprising a channel formed therein for placement of the electric wire therein, said channel placement based on a wire gauge associated with said channel such that said second end of said fiber optic cable is adjacent the wire insulation upon insertion of the electric wire.

20. Apparatus according to claim 19 wherein said at least one wire guide is interchangeable within said clamping fixture to accommodate range of wire gauges.

21. Apparatus according to claim 19 further comprising an IR sampling device at said second end of said fiber optic cable, said sampling device adjacent the wire insulation upon insertion of the electric wire.

22. Apparatus according to claim 19 wherein at least one of said wire guide channels comprises a semi-circular channel therein for placement of the wire, said semi-circular channels including a flat portion formed therein operable to engage the wire insulation as said spring-hinged clamping fixture begins to close and push against the wire insulation such that the wire insulation tends to move towards said second end of said fiber optic cable.

* * * * *